(12) United States Patent
Jin et al.

(10) Patent No.: US 11,033,252 B2
(45) Date of Patent: Jun. 15, 2021

(54) ULTRASOUND PROBE AND ULTRASOUND DIAGNOSIS SYSTEM INCLUDING SAME

(71) Applicant: SAMSUNG MEDISON CO., LTD., Gangwon-do (KR)

(72) Inventors: Gil-ju Jin, Gangwon-do (KR); Ho-san Han, Seoul (KR); Dong-hyun Kim, Gangwon-do (KR); Mi-Jeoung Ahn, Gangwon-do (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 404 days.

(21) Appl. No.: 16/073,736

(22) PCT Filed: Mar. 7, 2016

(86) PCT No.: PCT/KR2016/002223
§ 371 (c)(1),
(2) Date: Jul. 27, 2018

(87) PCT Pub. No.: WO2017/131280
PCT Pub. Date: Aug. 3, 2017

(65) Prior Publication Data
US 2019/0008486 A1      Jan. 10, 2019

(30) Foreign Application Priority Data
Jan. 28, 2016 (KR) .......................... 10-2016-0010716

(51) Int. Cl.
*A61B 8/00* (2006.01)
*A61B 8/14* (2006.01)
(Continued)

(52) U.S. Cl.
CPC ................ *A61B 8/546* (2013.01); *A61B 8/00* (2013.01); *A61B 8/08* (2013.01); *A61B 8/14* (2013.01);
(Continued)

(58) Field of Classification Search
CPC .... A61B 8/00; A61B 8/08; A61B 8/14; A61B 8/4405; A61B 8/4438; A61B 8/4444;
(Continued)

(56) References Cited

U.S. PATENT DOCUMENTS 8,574,159 B2   11/2013   Kondoh
9,383,435 B2   7/2016    Osawa
(Continued)

FOREIGN PATENT DOCUMENTS

CN        102525557 A    7/2012
JP        H10-085219 A   4/1998
(Continued)

OTHER PUBLICATIONS

Extended European Search Report dated Oct. 4, 2019 issued in European Patent Application No. 16888256.1.
(Continued)

*Primary Examiner* — Boniface N Nganga
(74) *Attorney, Agent, or Firm* — Morgan, Lewis & Bockius LLP

(57) ABSTRACT

Provided is an ultrasound probe. The ultrasound probe may maintain temperature of an acoustic module predetermined temperature or less even when an image processor is disposed in a rear direction of the acoustic module inside a housing. For purpose, the ultrasound probe may include at least one anisotropic heat conductive member such that heat from the acoustic module is transferred to a first heat sink member disposed in a rear direction of the image processor.

18 Claims, 17 Drawing Sheets

(51) Int. Cl.
*A61B 8/08* (2006.01)
*G01S 7/52* (2006.01)
*G10K 11/30* (2006.01)

(52) U.S. Cl.
CPC .......... *A61B 8/4444* (2013.01); *A61B 8/5207* (2013.01); *A61B 8/56* (2013.01); *G01S 7/52079* (2013.01); *G10K 11/30* (2013.01); *A61B 8/4405* (2013.01); *A61B 8/4438* (2013.01); *A61B 8/4472* (2013.01)

(58) Field of Classification Search
CPC ..... A61B 8/4472; A61B 8/5207; A61B 8/546; A61B 8/56; G01S 7/52079; G10K 11/30
See application file for complete search history.

(56) References Cited

U.S. PATENT DOCUMENTS

| | | | | |
|---|---|---|---|---|
| 2002/0182397 | A1* | 12/2002 | Whatley | H01L 23/373 428/297.4 |
| 2007/0167807 | A1* | 7/2007 | Takeuchi | A61B 8/12 600/459 |
| 2008/0188755 | A1* | 8/2008 | Hart | A61B 8/546 600/459 |
| 2008/0312537 | A1 | 12/2008 | Hyuga | |
| 2012/0150038 | A1 | 6/2012 | Osawa | |
| 2013/0085396 | A1 | 4/2013 | Isono et al. | |
| 2013/0286593 | A1* | 10/2013 | Cho | G01N 29/326 361/707 |
| 2013/0303918 | A1 | 11/2013 | Miyajima et al. | |
| 2014/0364741 | A1* | 12/2014 | Cho | A61B 8/4427 600/459 |
| 2014/0364742 | A1* | 12/2014 | Cho | A61B 8/4444 600/459 |
| 2015/0253290 | A1 | 9/2015 | Fujii et al. | |
| 2015/0289852 | A1 | 10/2015 | Cho et al. | |
| 2016/0007957 | A1* | 1/2016 | Murphy | A61B 8/546 600/459 |
| 2017/0020490 | A1* | 1/2017 | Ryu | A61B 8/4444 |
| 2017/0188995 | A1* | 7/2017 | Bruestle | A61B 8/4427 |

FOREIGN PATENT DOCUMENTS

| | | | |
|---|---|---|---|
| JP | 2006-025892 | A | 2/2006 |
| JP | 2008-022077 | A | 1/2008 |
| JP | 2008-311700 | A | 12/2008 |
| JP | 2009-297352 | A | 12/2009 |
| JP | 2013-052023 | A | 3/2013 |
| JP | 2006-129965 | A | 7/2016 |
| KR | 10-2010-0122060 | A | 11/2010 |
| KR | 10-2013-0035213 | A | 4/2013 |
| KR | WO-2015129938 | A1 * | 9/2015 |
| KR | 10-2015-0118496 | A | 10/2015 |
| WO | 2015/147355 | A1 | 10/2015 |

OTHER PUBLICATIONS

Written Opinion and International Search Report dated Oct. 26, 2016 issued in International Patent Application No. PCT/KR2016/002223 (with Englilsh translation).
Chinese Office Action dated Sep. 25, 2020 issued in Chinese Patent Application No. 201680080513.5 (with English translation).

* cited by examiner

ULTRASOUND PROBE AND ULTRASOUND DIAGNOSIS SYSTEM INCLUDING SAME

CROSS REFERENCE

This patent application is the U.S. National Phase under 35 U.S.C. § 371 of International Application No. PCT/KR2016/002223, filed on Mar. 7, 2016, which claims the benefit of Korean Patent Application No. 10-2016-0010716, filed on Jan. 28, 2016, the entire contents of each are hereby incorporated by reference.

TECHNICAL FIELD

The present disclosure relates to an ultrasound probe used for ultrasound diagnosis and an ultrasound diagnosis system including the same.

BACKGROUND ART

An ultrasound diagnosis system is an apparatus configured to diagnose an examinee by imaging an inside of an object of the examinee, and irradiates an ultrasound signal to the object and receives information of an echo signal reflected from the object, thereby obtaining an image of a predetermined portion inside the object.

Since the ultrasound diagnosis system has advantages of high safety compared with a diagnosis apparatus that uses an X-ray, displaying an image in real-time, and being safe because there is no exposure to radioactivity, the ultrasound diagnosis system is widely in use together with other imaging diagnosis apparatuses.

The ultrasound diagnosis system includes an ultrasound probe contacting an object to make a contrasted image of the inside of a body of the object. The ultrasound probe includes an ultrasound transceiver responsible for generating and transmitting/receiving an ultrasound signal therein. During an ultrasound diagnosing process, the ultrasound transceiver contacts the object.

The ultrasound transceiver contacting an object may generate heat during its operation. Depending on a case, temperature of the ultrasound transceiver becomes higher than temperature of the object and may make the object unpleasant, and in a severe case, may cause a burn to the object.

As an attempt to prevent this, the ultrasound probe may include a heat sink member configured to discharge heat of the ultrasound transceiver backward, not forward facing the object.

To reduce a size of a transmitted file when the ultrasound probe transmits the file to an external apparatus, for example, a diagnosis apparatus having a display, an image processor for processing an image may be disposed inside the ultrasound probe. The image processor may generate heat during its operation and may have a higher temperature than temperature of the ultrasound transceiver.

Therefore, even though the heat sink member that discharges heat of the ultrasound transceiver is disposed inside the ultrasound probe, the heat sink member may not perform its proper function due to the image processor, and rather, the ultrasound transceiver may be heated by the image processor.

DESCRIPTION OF EMBODIMENTS

Technical Problem

Provided are an ultrasound probe and an ultrasound diagnosis system including the same which may maintain temperature of an ultrasound transceiver at a predetermined temperature or less with a slim structure even though an image processor having a high temperature is disposed inside the ultrasound probe.

Solution to Problem

According to an aspect of the present disclosure, an ultrasound probe includes: a housing; an acoustic module disposed inside the housing, and configured to transmit an ultrasound signal to an object and receive an echo signal reflected from the object; an image processor disposed in a rear direction of the acoustic module inside the housing, electrically connected to the acoustic module, and configured to generate ultrasound image data from the echo signal received from the acoustic module; a first insulating wall disposed between the acoustic module and the image processor inside the housing; a first heat sink member disposed in a rear direction of the image processor inside the housing; and at least one anisotropic heat conductive member passing through the first insulating wall to connect the acoustic module with the first heat sink member, and configured such that a heat conductivity thereof in a lengthwise direction of the housing is greater than a heat conductivity thereof in a direction perpendicular to the lengthwise direction of the housing to transfer heat of the acoustic module to the first heat sink member.

While the ultrasound probe operates, a temperature of the image processor may be higher than a temperature of the acoustic module.

The anisotropic heat conductive member may be configured such that the heat conductivity thereof in the lengthwise direction of the housing is ten times greater than the heat conductivity thereof in the direction perpendicular to the lengthwise direction of the housing.

The anisotropic heat conductive member may be configured such that the heat conductivity thereof in the lengthwise direction of the housing is 50 W/mK or more, and the heat conductivity thereof in the direction perpendicular to the lengthwise direction of the housing is 0.5 W/mK or less.

The anisotropic heat conductive member may include at least one heat conductive fiber and an insulating material surrounding the at least one heat conductive fiber.

A diameter of the heat conductive fiber may be 15 μm or less.

A thickness of the anisotropic heat conductive member may be 5 mm or less.

At least a portion of the anisotropic heat conductive member may be disposed between the image processor and an outer wall of the housing.

At least a portion of the anisotropic heat conductive member may be disposed inside an outer wall of the housing.

The acoustic module may include: a piezoelectric body configured to generate an ultrasound signal; an acoustic lens disposed in front of the piezoelectric body; a backing plate disposed in a rear direction of the piezoelectric body; and a heat sink member configured to discharge heat of the piezoelectric body, wherein one end of the anisotropic heat conductive member contacts the heat sink member.

The ultrasound probe may further include a heat conductive material disposed between the acoustic module and the anisotropic heat conductive member.

The ultrasound probe may further include: a second heat sink member disposed in a rear direction of the housing; and a heat conductive plate disposed between the image processor and the second heat sink member.

A second insulating wall configured to block heat transfer between the first heat sink member and the second heat sink member may be disposed in a rear direction of the housing.

The housing may include a heat sink portion having a mesh structure through which air flows in/out, and the first heat sink member may be disposed inside the heat sink portion.

The anisotropic heat conductive member may be provided as a plurality of anisotropic heat conductive members, and the plurality of anisotropic heat conductive members may be spaced apart from each other in a width direction of the housing.

The ultrasound probe may be a wireless ultrasound probe.

According to another aspect of the present disclosure, an ultrasound diagnosis system may include the ultrasound probe.

Advantageous Effects of Disclosure

An ultrasound probe and an ultrasound diagnosis system including the same according to embodiments may maintain a temperature of an ultrasound transceiver at a predetermined temperature or less with a slim structure even though the ultrasound probe includes an image processor heated to a high temperature therein.

MODE OF DISCLOSURE

Figure 1:
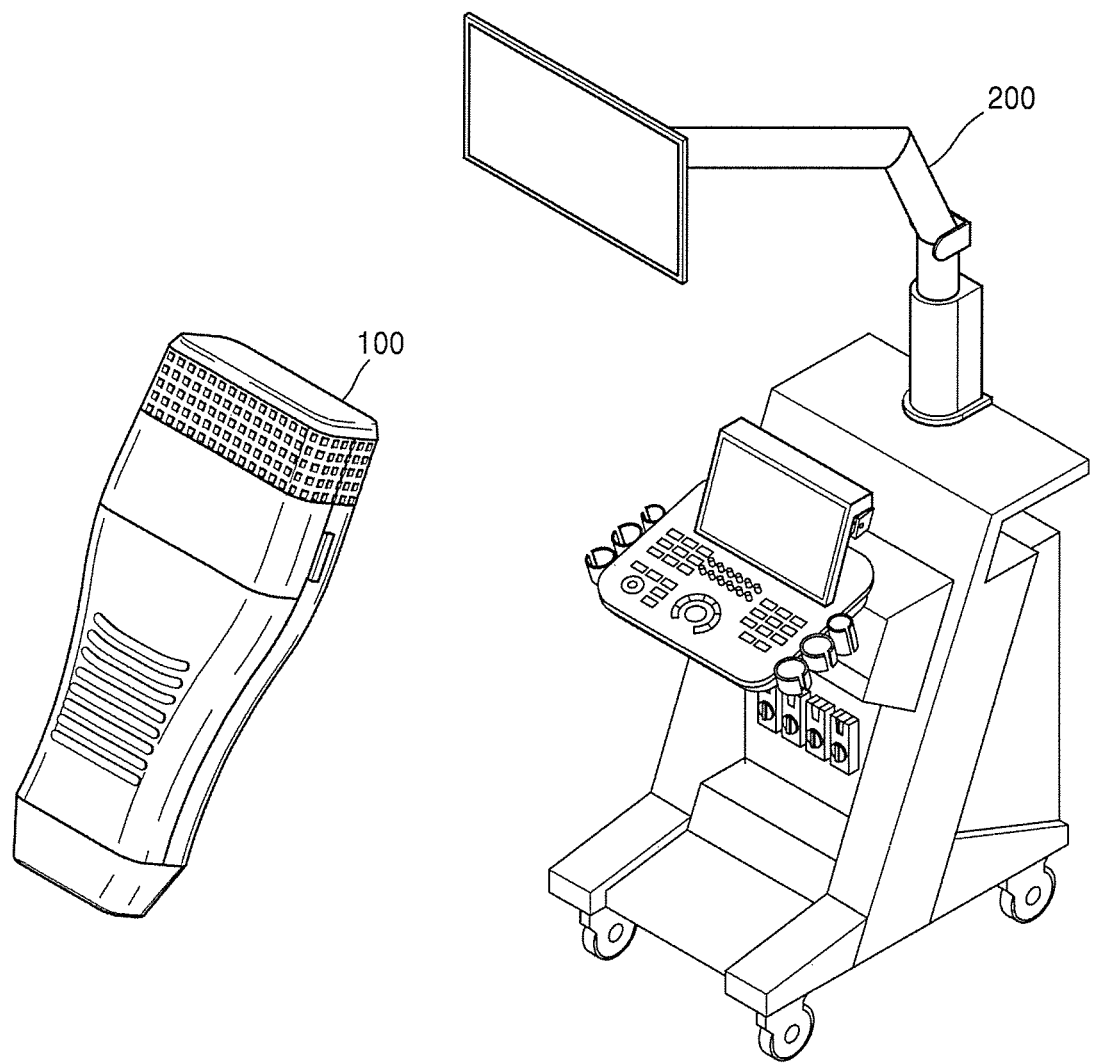
FIG. 1 is a view for explaining an ultrasound diagnosis system according to an embodiment.

Advantages and characteristics of the present disclosure, and methods of accomplishing them may be apparent when referring to embodiments below together with accompanying drawings. However, the present disclosure is not limited to the embodiments below and may be implemented in various different forms, and the present embodiments are provided to make the present disclosure complete and give complete understanding of the scope of the present disclosure to those of ordinary skill in the art. The present disclosure is only defined by claims.

Terms used for the present specification are briefly explained, and the present disclosure is described specifically.

As the terms used herein, so far as possible, widely-used general terms are selected in consideration of functions in the present disclosure; however, these terms may vary according to the intentions of those of ordinary skill in the art, the precedents, or the appearance of new technology. Also, in some cases, there may be terms that are arbitrarily selected by the applicant, and the meanings thereof will be described in detail in the corresponding portions of the description of the present disclosure. Therefore, the terms used herein are not simple titles of terms and should be defined based on the meanings thereof and the overall description of the present disclosure.

Throughout the specification, when a portion "includes" an element, another element may be further included, rather than excluding the existence of the other element, unless otherwise described. Also, a term "unit" used in the specification denotes a software and a hardware element such as a field-programmable gate array (FPGA) or an application specific integrated circuit (ASIC), and a "unit" performs certain roles. However, a "unit" is not limited to software or hardware. A "unit" may be configured to exist in a storage medium which may be addressed or may be configured to reproduce one or more processors. Therefore, as an example, a "unit" includes elements such as software elements, object-oriented software elements, class elements, and task elements, processes, functions, characteristics, procedures, sub-routines, segments of a program code, drivers, firmware, a micro code, a circuit, data, a database, data structures, tables, arrays, and variables. A function provided in elements and "units" may be coupled to a smaller number of elements and "units", or may be further separated as additional elements or "units".

An "ultrasound image" throughout the specification denotes an image of an object obtained by using an ultrasound wave. Also, an "object" may include a human or an animal, or a part thereof. For example, the object may include at least one of an organ such as a liver, a heart, a womb, a brain, a breast, an abdomen, and a blood vessel. Also, the object may be a phantom. The phantom may denote a material which very approximates density and an effective atomic number of living things, and very approximates a volume of living things. For example, the phantom may be a spherical phantom having a similar characteristic to a human body.

Also, throughout the specification, a "user" may be a medical expert and may be a doctor, a nurse, a medical laboratory technologist, a medical image expert, etc. and may be an engineer who repairs a medical apparatus, and is not limited thereto.

Also, in the present specification, expressions such as a "first", a "second", a "1-1st" are terms exemplarily used to indicate different elements, entities, images, pixels or patches. Therefore, expressions such as a "first", a "second", a "1-1st" do not represent a sequence or a priority between elements.

Hereinafter, embodiments of the present disclosure are described in detail with reference to accompanying drawing to enable those of ordinary skill in the art to easily carry out the present disclosure. Also, for clear description of the present disclosure, parts not related to descriptions are omitted in the drawings.

FIG. 1 is a view for explaining an ultrasound diagnosis system according to an embodiment. Referring to FIG. 1, a wireless ultrasound probe 100 and an ultrasound diagnosis apparatus 200 may constitute the ultrasound diagnosis system.

The wireless ultrasound probe 100 may transmit an ultrasound signal to an object and receive an echo signal reflected from the object to generate a received signal. The wireless ultrasound probe 100 may generate ultrasound image data by image-processing the received signal. The wireless ultrasound probe 100 may transmit the generated ultrasound image data to the ultrasound diagnosis apparatus 200. The wireless ultrasound probe 100 may be wirelessly connected with the ultrasound diagnosis apparatus 200 by using wireless communication.

The ultrasound diagnosis apparatus 200 may be wirelessly connected with the wireless ultrasound probe 100, and may display an ultrasound image by using the ultrasound image data received from the wireless ultrasound probe 100. For example, the ultrasound diagnosis apparatus 200 may display not only an ultrasound image of a gray scale obtained by scanning an object according to an amplitude (A) mode, a brightness (B) mode, and a motion (M) mode, but also movements of the object as a Doppler image. In an embodiment, the ultrasound diagnosis apparatus 200 may be configured in a cart form and a portable form, and may include a picture archiving and communication system (PACS) viewer, hand-carried cardiac ultrasound (HCU) equipment, a smartphone, a laptop computer, a personal digital assistant (PDA), a tablet personal computer (PC), etc., and is not limited thereto.

In an embodiment, the ultrasound diagnosis apparatus 200 may be an apparatus configured to generate an ultrasound image by processing the ultrasound image data received from the wireless ultrasound probe 100, and display the generated image, or an apparatus configured to implement only an image-displaying function simply without a separate image processing function. That is, the ultrasound diagnosis apparatus 200 may include a display configured to receive an image from the wireless ultrasound probe 100 and display the received image on a screen without additional processing.

The wireless ultrasound probe 100 may be wirelessly connected with the ultrasound diagnosis apparatus 200 by using data communication. In an embodiment, the wireless ultrasound probe 100 may be wirelessly connected with the ultrasound diagnosis apparatus 200 by using short distance wireless communication of a 60 GHz mm wave. However, the wireless ultrasound probe 100 is not limited thereto and may be connected with the ultrasound diagnosis apparatus 200 by using at least one of data communications including a wireless local area network (LAN), Wi-Fi, Bluetooth, Zigbee, Wi-Fi direct (WFD), ultra wideband (UWB), infrared data association (IrDA), Bluetooth low energy (BLE), near filed communication (NFC), wireless broadband Internet (Wibro), world interoperability for microwave access (WiMAX), shared wireless access protocol (SWAP), wireless gigabit alliance (WiGig), and RF communication.

Figure 2:
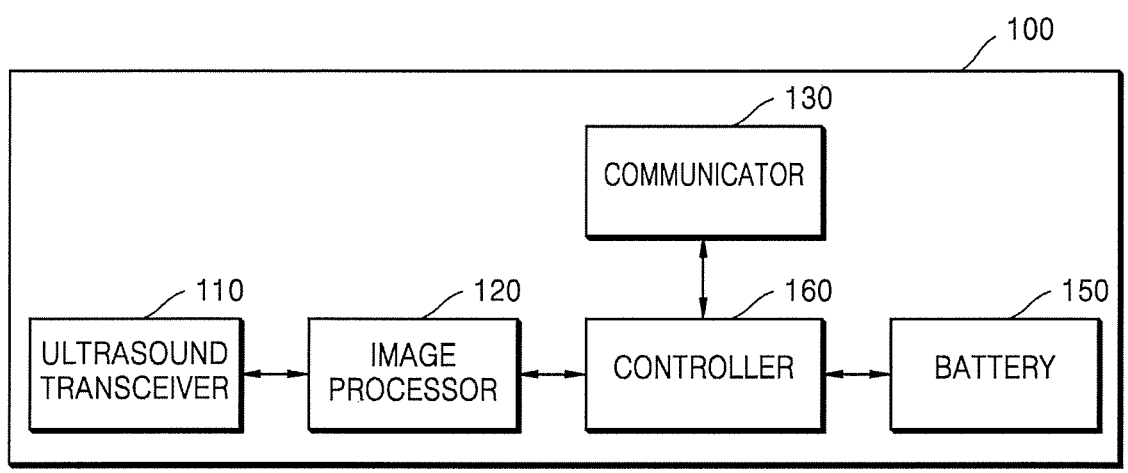
FIG. 2 is a block diagram of a configuration of a wireless ultrasound probe according to an embodiment.

FIG. 2 is a block diagram of a configuration of the wireless ultrasound probe 100 according to an embodiment.

Referring to FIG. 2, the wireless ultrasound probe 100 may include an ultrasound transceiver 110, an image processor 120, a communicator 130, a battery 150, and a controller 160.

The ultrasound transceiver 110 transmits an ultrasound signal to an object and receives an echo signal reflected from the object. The ultrasound transceiver 110 may generate a pulse for forming a transmission ultrasound wave corresponding to a predetermined pulse repetition frequency (PRF). The ultrasound transceiver 110 may apply a delay time for determining transmission directionality to a pulse. Delay time-applied pulses may respectively correspond to a plurality of piezoelectric vibrators included in a transducer. The ultrasound transceiver 110 may transmit an ultrasound signal to an object by applying pulses corresponding to the plurality of piezoelectric vibrators at timings respectively corresponding to the delay time-applied pulses.

The image processor 120 generates ultrasound image data corresponding to a kind of data determined by the controller 160 from the echo signal received from the ultrasound transceiver 110. The image processor 120 may generate ultrasound image data by processing the echo signal reflected from the object. The image processor 120 may amplify the echo signal for each channel, and analog-digital (AD) convert the amplified echo signal. The image processor 120 may apply a delay time for determining reception directionality to the digital-converted echo signal. Likewise, since the image processor 120 is included in the wireless ultrasound probe 100, a capacity of data transmitted by the communicator 130 may be reduced.

The communicator 130 transmits the ultrasound image data generated by the image processor 120 to the ultrasound diagnosis apparatus 200 (see FIG. 1). In an embodiment, the communicator 130 may transmit raw data generated by analog-digital converting the echo signal amplified by the image processor 120, to the ultrasound diagnosis apparatus 200. In an embodiment, the communicator 130 may transmit at least one of setting information of the wireless ultrasound probe 100 including identification information of the wireless ultrasound probe 100, ultrasound preset setting information, information about a user of the wireless ultrasound probe 100, and information about an object, to the ultrasound diagnosis apparatus 200.

The communicator 130 may perform wireless communication with the ultrasound diagnosis apparatus 200. The communicator 130 may perform data communication with the ultrasound diagnosis apparatus 200 by using at least one of short distance communications including a wireless LAN, Wi-Fi, Bluetooth, Zigbee, WFD, IrDA, BLE, NFC, Wibro, WiMax, SWAP, WiGig, and RF communication. In an embodiment, the communicator 130 may perform data communication with the ultrasound diagnosis apparatus 200 by using a short distance communication of a 60 GHz mm wave.

In an embodiment, the communicator 130 may be connected with a network via a wired line or wirelessly to communicate with an external device or server. The communicator 130 may give and take data to and from a hospital server or another medical apparatus inside the hospital connected through a PACS. Also, the communicator 130 may perform data communication according to digital imaging and communications in medicine (DICOM).

The communicator 130 may transmit/receive data related to a diagnosis of an object such as an ultrasound image, ultrasound data, Doppler data, etc. of the object and also transmit/receive a medical image captured by other medical apparatuses such as a CT, an MRI, and an X-ray through a network. Furthermore, the communicator 130 may receive information about a diagnosis history or a treatment schedule of a patient, etc. from a server and utilize the same in diagnosing the object. The communicator 130 may perform data communication with a portable terminal of a doctor or a customer as well as a server or a medical apparatus inside a hospital.

The battery 150 supplies power required for the wireless ultrasound probe 100 to operate. The battery 150 may include at least one of Li-ion, nickel metal hydride (Ni-MH), PbOx, and Na-S. However, the battery 150 is not limited thereto and may include a rechargeable substance and/or material such as a lithium metal oxide, an organic electrode material, and a transition metal.

The controller 160 controls the communicator 130 to determine data communication used for transmitting ultrasound image data generated by the image processor 120 to the ultrasound diagnosis apparatus 200.

The controller 160 may determine at least one of wireless communication used by the ultrasound diagnosis apparatus 200, an available bandwidth, a transmission speed through a communication channel, a kind of a communication channel, and an identifier of the ultrasound diagnosis apparatus 200 based on information about the ultrasound diagnosis apparatus 200.

In an embodiment, the controller 160 may select at least one image processing operation based on a determined kind of data among a plurality of sequential image processing operations that should be performed to generate a displayable ultrasound image from an echo signal. In an embodiment, the controller 160 may obtain information about the ultrasound diagnosis apparatus 200 through the communicator 130. The controller 160 may determine a kind of data which the ultrasound diagnosis apparatus 200 is configured to process based on the information about the ultrasound diagnosis apparatus 200, and determine a method through which the wireless ultrasound probe 100 communicates with the ultrasound diagnosis apparatus 200. For example, the controller 160 may control the communicator 130 to use the short distance communication of a 60 GHz mm wave when transmitting raw data generated by analog-digital converting, at the image processor 120, an echo signal reflected from an object, to the ultrasound diagnosis apparatus 200.

The controller 160 may be configured as a module including at least one of, for example, a central processing unit, a microprocessor, a graphic processing unit, a random access memory (RAM), and a read only memory (ROM). In an embodiment, the controller 160 may be implemented as an application processor (AP). In an embodiment, the controller 160 may be implemented as a hardware element such as a FPGA or an ASIC. However, the controller 160 is not limited thereto. The controller 160 may include elements such as software elements, object-oriented software elements, class elements, and task elements, processes, functions, characteristics, procedures, sub-routines, segments of a program code, drivers, firmware, a micro code, a circuit, data, a database, data structures, tables, arrays, and variables.

Figure 3:
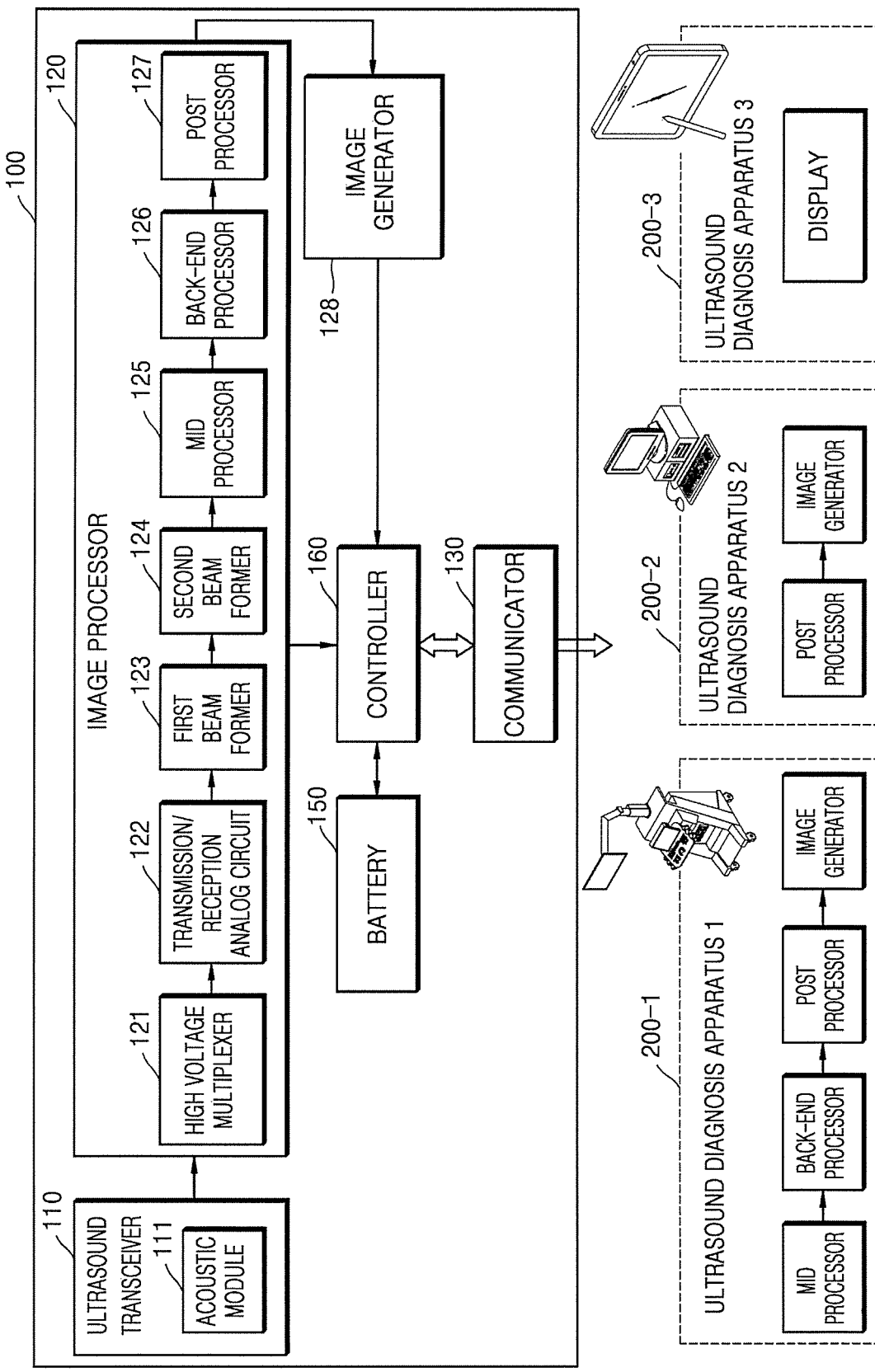
FIG. 3 is a conceptual view for explaining a method in which a wireless ultrasound probe communicates with an ultrasound diagnosis apparatus by using a plurality of wireless communications.

FIG. 3 is a conceptual view for explaining a method in which the wireless ultrasound probe 100 communicates with the ultrasound diagnosis apparatus 200 by using a plurality of wireless communications.

Referring to FIG. 3, the wireless ultrasound probe 100 may include the ultrasound transceiver 110, the image processor 120, an image generator 128, the communicator 130, and the controller 160. However, a configuration of the wireless ultrasound probe 100 according to an embodiment is not limited to the elements shown in FIG. 3. The wireless ultrasound probe 100 may include the number of elements greater or less than the number of elements shown in FIG. 3. Since the communicator 130 and the controller 160 are the same as the communicator 130 and the controller 160 shown in FIG. 2, descriptions thereof are omitted.

The ultrasound transceiver 110 may include an acoustic module 111. The acoustic module 111 receives an echo signal reflected from an object. The acoustic module 111 may include a plurality of transducers. The plurality of transducers may vibrate depending on an electric signal transferred thereto, generate an ultrasound wave, which is acoustic energy, and generate an electric signal by processing acoustic energy reflected from an object.

The image processor 120 may include a high voltage multiplexer (HV mux) 121, a transmission/reception (T/RX) analog circuit 122, a first beam former 123, a second beam former 124, a mid processor 125, a back-end processor 126, and a post processor 127.

The HV mux 121 may sequentially select the plurality of transducers of the acoustic module 111. The T/RX analog circuit 122 may divide ultrasound signals into signals to be transmitted to an object, and signals obtained by processing echo signals received from the object.

The beam formers 123 and 124 perform a process of focusing on an echo signal to see a reflection characteristic of a tissue of an object at a desired location from a received echo signal. In an embodiment, the first beam former 123 may be an analog beam former, and the second beam former 124 may be a digital beam former.

The mid processor 125 may perform an intermediate processing operation on a signal which is beam-formed by the beam formers 123 and 124. For example, the mid processor 125 may control a gain of a beam-formed signal. The mid processor 125 may perform phase rotation corresponding to dynamic frequency variation on each of a plurality of regions separated based on predetermined depths in order to compensate for a frequency variation that changes depending on a depth of an object. Also, the mid processor 125 may perform low-pass filtering.

The back-end processor 126 may detect envelopes of I-component data and Q-component data output from the mid processor 125.

The post processor 127 may perform digital signal processing (DSP) for generating a Doppler (D)-mode image and a color (C)-mode image.

The image generator 128 may generate an image of a form which may be output on a screen from a processed signal.

In an embodiment, a plurality of ultrasound diagnosis apparatuses 200-1, 200-2, and 200-3 may respectively have different kinds of data which may be processed in the inside. That is, generally, the plurality of ultrasound diagnosis apparatuses 200-1, 200-2, and 200-3 may be configured to generate an ultrasound image from an intermediate signal or image data obtained from one of the described image processing elements 121 to 127. Each of the elements 121 to 127 included in the image processor 120 may be the image processor 120 of the wireless ultrasound probe 100 according to an embodiment. Therefore, the wireless ultrasound probe 100 according to an embodiment may output data suitable for the ultrasound diagnosis apparatuses 200-1, 200-2, and 200-3 depending on kinds of data which may be processed by the ultrasound diagnosis apparatuses 200-1, 200-2, and 200-3 such that the wireless ultrasound probe 100 is connected with the various ultrasound diagnosis apparatuses 200-1, 200-2, and 200-3.

The controller 160 may recognize an identifier of an ultrasound diagnosis apparatus connected with the wireless ultrasound probe 100 among the plurality of ultrasound diagnosis apparatuses 200-1, 200-2, and 200-3. The wireless ultrasound probe 100 may recognize a signal processing procedure which may be processed by the ultrasound diagnosis apparatus based on the identifier of the ultrasound diagnosis apparatus, and perform, inside the wireless ultrasound probe 100, a signal processing procedure which cannot be performed by the ultrasound diagnosis apparatus. Transmission data transmitted from the wireless ultrasound probe 100 to the ultrasound diagnosis apparatus may be an intermediate processed result or processing-completed image data. The ultrasound diagnosis apparatus may perform residual processing operations, which are not completed, on the transmission data to generate an ultrasound image to output on a screen or a display.

The wireless ultrasound probe 100 may selectively output intermediate data generated in an arbitrary operation among a series of processing operations for obtaining an ultrasound image of an object from an echo signal received from the object based on the identifier of the ultrasound diagnosis apparatus.

In an embodiment, the first ultrasound diagnosis apparatus 200-1 may perform all of signal processing operations except beam forming. Therefore, in the case where the wireless ultrasound probe 100 is connected to the first ultrasound diagnosis apparatus 200-1, the wireless ultrasound probe 100 may transmit a signal, as transmission data, output from the second beam former 124 to the first ultrasound diagnosis apparatus 200-1. In this case, the wireless ultrasound probe 100 may inactivate the mid processor 125, the back-end processor 126, the post processor 127, and the image generator 128 which perform processing operations after the beam forming.

In an embodiment, in the case where the second ultrasound diagnosis apparatus 200-2 may perform processing operations after the back-end processor 126 in order to display an ultrasound image, the wireless ultrasound probe 100 may generate an output from the back-end processor 126 as transmission data. In this case, since the wireless ultrasound probe 100 does not need to perform functions of the post processor 127 and the image generator 128, the wireless ultrasound probe 100 may inactivate the post processor 127 and the image generator 128.

Unlike the first ultrasound diagnosis apparatus 200-1 and the second ultrasound diagnosis apparatus 200-2, the third ultrasound diagnosis apparatus 200-3 is an apparatus configured to simply implement only an image display function without a separate image processing function. Therefore, in the case where the wireless ultrasound probe 100 is connected to the third ultrasound diagnosis apparatus 200-3, the wireless ultrasound probe 100 may transmit a signal, as transmission data, output from the image generator 128 to the third ultrasound diagnosis apparatus 200-3.

In an embodiment, the wireless ultrasound probe 100 may transmit ultrasound image data to the ultrasound diagnosis apparatuses 200-1, 200-2, and 200-3 by using a plurality of data communications. The wireless ultrasound probe 100 may transmit transmission data by using suitable data communication depending on wireless communication used by the ultrasound diagnosis apparatuses 200-1, 200-2, and 200-3. In an embodiment, the wireless ultrasound probe 100 may use different data communications depending on a characteristic of data to transmit.

Figure 4A:
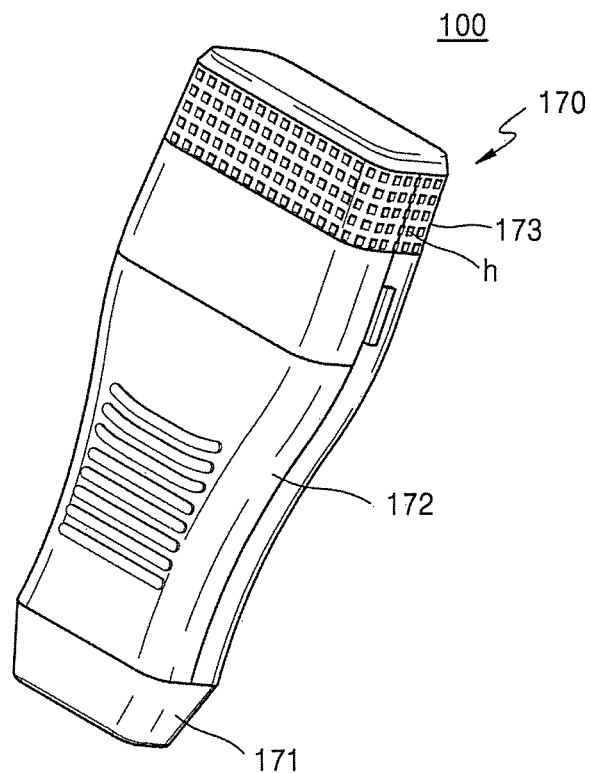
FIGS. 4A and 4B are a perspective view and a side view of a wireless ultrasound probe according to an embodiment.
Figure 4B:
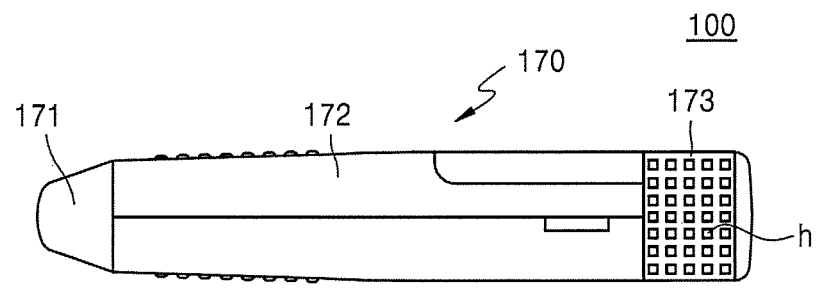
Figure 5:
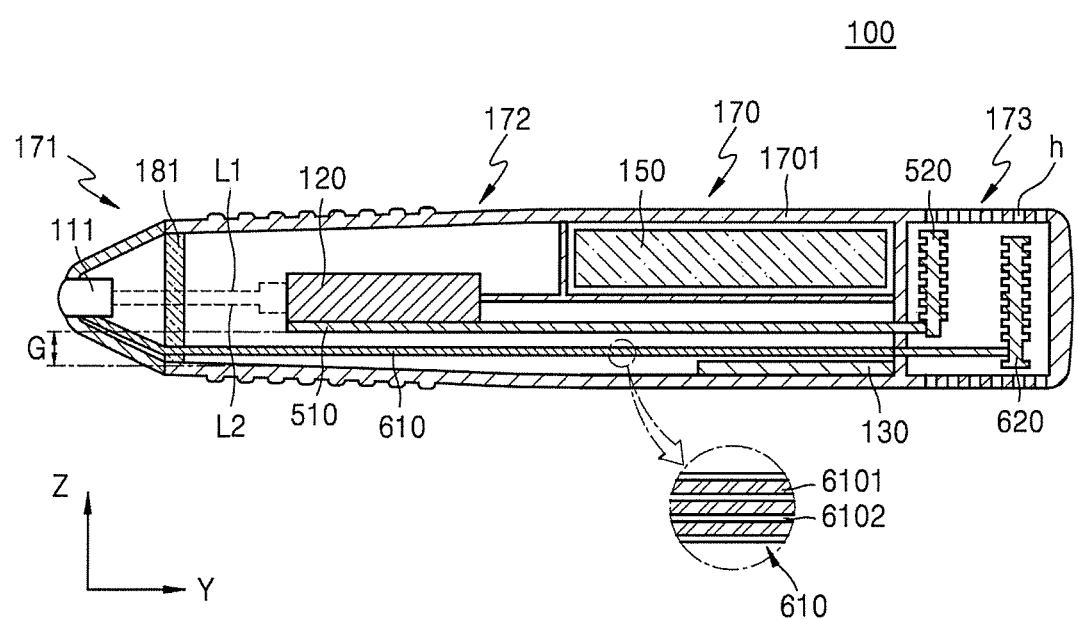
FIG. 5 is a view for explaining an inner configuration of a wireless ultrasound probe according to an embodiment.

FIGS. 4A and 4B are a perspective view and a side view of the wireless ultrasound probe 100 according to an embodiment, and FIG. 5 is a view for explaining an inner configuration of the wireless ultrasound probe 100 according to an embodiment.

Referring to FIGS. 4A, 4B, and 5, the wireless ultrasound probe 100 includes a housing 170. The housing 170 forms an appearance of the wireless ultrasound probe 100 and includes a head portion 171, a handle portion 172, and a heat sink portion 173.

The housing 170 has a predetermined length in a lengthwise direction, for example, a Y-direction, and has a predetermined height in a height direction, for example, an X-direction.

The head 171 portion is disposed in a front direction of the handle 172 portion, and the heat sink portion 173 is disposed in a rear direction of the handle portion 172. Here, the front direction may be a direction facing an object, and the rear direction may be an opposite direction of the front direction.

The ultrasound transceiver 110, the image processor 120, the communicator 130, the battery 150, and the controller 160 may be disposed inside the housing 170. For example, the acoustic module 111 of the ultrasound transceiver 110 may be disposed inside the head portion 171. The image processor 120, the communicator 130, and the battery 150 may be disposed inside the handle portion 172. The image processor 120 may be disposed in a front direction of the communicator 130 and the battery 150 inside the handle portion 172.

The image processor 120 is disposed in a rear direction of the acoustic module 111 and electrically connected to the acoustic module 111. The image processor 120 is electrically connected with the acoustic module 111 by using at least one signal line. For example, the image processor 120 is electrically connected with the acoustic module 111 by using two signal lines L1 and L2. The image processor 120 may include the beam formers 123 and 124 (see FIG. 3).

While the wireless ultrasound probe 100 operates, heat may occur from the elements disposed inside the housing 170. For example, while ultrasound diagnosis is performed through the wireless ultrasound probe 100, heat may occur from the acoustic module 111 and the image processor 120 disposed inside the housing 170. For example, while the acoustic module 111 transmits an ultrasound signal or receives an echo signal, temperature of the acoustic module 111 may rise. While the image processor 120 performs an image processing operation, temperature of the image processor 120 may rise.

Figure 6A:
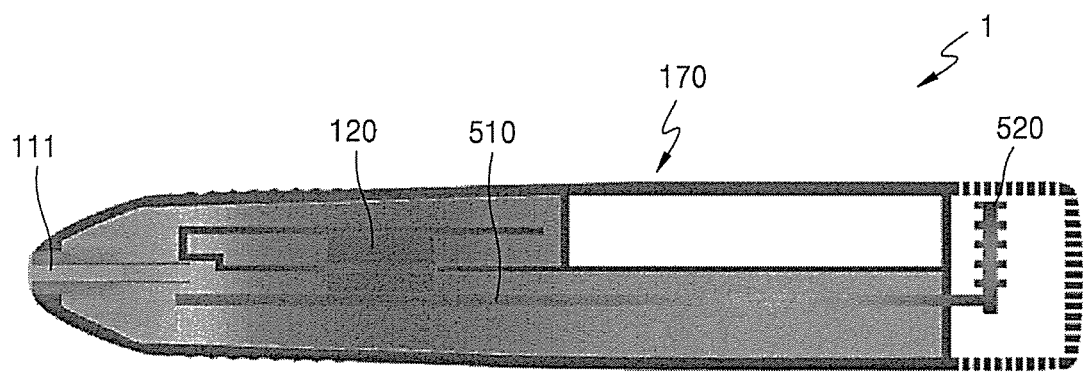
FIG. 6A is a view for explaining temperature distribution when an acoustic module and an image processor of a wireless ultrasound probe according to a comparative example emit heat.
Figure 6B:
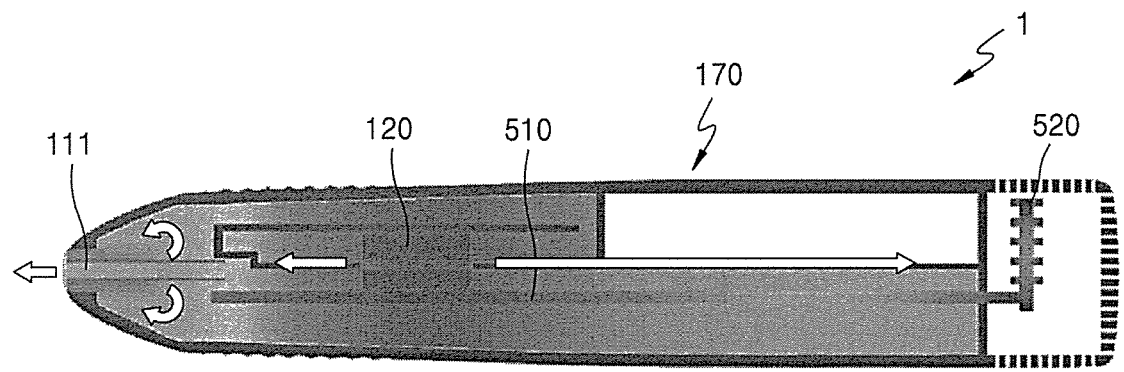
FIG. 6B is a view for explaining a heat transfer direction in FIG. 6A.

FIG. 6A is a view for explaining temperature distribution when the acoustic module 111 and the image processor 120 of a wireless ultrasound probe 1 according to a comparative example emit heat, and FIG. 6B is a view for explaining a heat transfer direction in FIG. 6A.

Referring to FIG. 6A, temperature of the image processor 120 may rise higher than temperature of the acoustic module 111. For example, heat may be generated from the acoustic module 111 and the temperature of the acoustic module 111 may rise to 40° C. to 50° C., and heat may be generated from the image processor 120 and the temperature of the image processor 111 may rise to 80° C. to 100° C.

Referring to FIG. 6B, since the temperature of the acoustic module 111 is less than the temperature of the image processor 120, heat generated from the image processor 120 may be transferred in a front direction and a rear direction. In contrast, heat generated from the acoustic module 111 cannot be transferred in a rear direction and rather may be transferred in a front direction.

Figure 7:
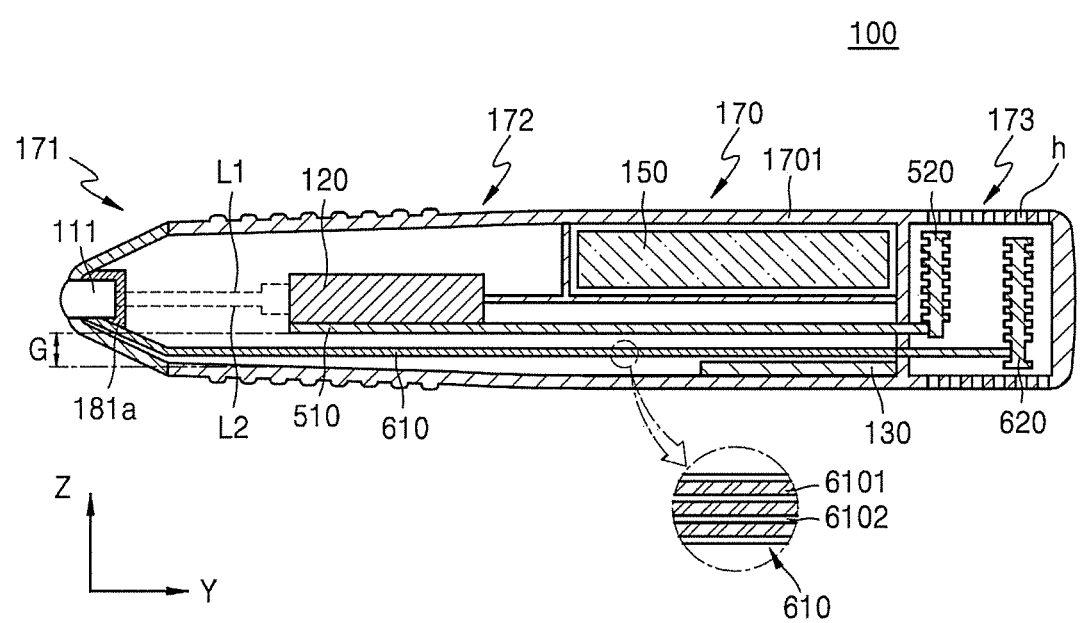
FIG. 7 is a conceptual cross-sectional view of a wireless ultrasound probe according to another embodiment.

Referring to FIG. 5 again, a first insulating wall 181 may be disposed between the acoustic module 111 and the image processor 120. The first insulating wall 181 may prevent the acoustic module 111 from being heated by the image processor 120. The first insulating wall 181 may prevent the acoustic module 111 from being radiant-heated by the image processor 120. The first insulating wall 181 may be disposed between the head portion 171 and the handle portion 172. However, the arrangement of the first insulating wall 181 is not limited thereto. For example, as illustrated in FIG. 7, a first insulating wall 181a may surround the acoustic module 111 inside the head portion 171.

To limit a temperature rise of the image processor 120 from which heat is generated, the wireless ultrasound probe 100 according to an embodiment may have a structure of discharging heat generated from the image processor 120 to the outside of the housing 170. For example, the wireless ultrasound probe 100 may include a heat conductive plate 510 and a second heat sink member 520 disposed inside the housing 170.

The heat conductive plate 510 contacts the image processor 120 inside the head handle portion 172. Accordingly, heat is transferred from the image processor 120 to the heat conductive plate 510 by heat conduction.

The heat conductive plate 510 extends in the lengthwise direction (Y-direction) of the housing 170, and the second heat sink member 520 is disposed at one end of the heat conductive plate 510.

The second heat sink member 520 is disposed inside the heat sink portion 173. The heat sink portion 173 may have a mesh structure including a plurality of holes h through which air may flow in and out. Therefore, with the heat sink portion 173 having the mesh structure, the second heat sink member 520 may be exposed to air and simultaneously may prevent a contact of a user. The second heat sink member 520 may include a plurality of radiating pins to increase an exposed area.

The image processor 120 is connected with the second heat sink member 520 by using the heat conductive plate 510. While the image processor 120 operates, the temperature of the image processor 120 gets higher than the temperature of the second heat sink member 520. Therefore, heat is transferred from the image processor 120, which is relatively high temperature, to the second heat sink member 520, which is relatively low temperature, through the heat conductive plate 510. The heat transferred to the second heat sink member 520 is discharged to air.

The heat conductive plate 510 and the second heat sink member 520 may prevent an external surface of the handle portion 172, which receives the image processor 120, from being heated to a predetermined temperature or more. For example, even when heat is generated during an operation of the image processor 120, the external surface of the handle portion 172 may be maintained at 43° C. or less. Therefore, a user may hold the handle portion 172 without inconvenience and perform an ultrasound diagnosis.

Also, the acoustic module 111 of the ultrasound transceiver 110 is a portion contacting an object when the wireless ultrasound probe 100 is normally used. Therefore, to prevent inconvenience or a burn of an object contacting the acoustic module 111, it may be important to maintain the temperature of the acoustic module 111 at a predetermined temperature or less. For example, it may be important to maintain the temperature of the acoustic module 111 at 43° C. or less.

To maintain the temperature of the acoustic module 111 at a predetermined temperature or less, for example, 43° C. or less, the wireless ultrasound probe 100 according to an embodiment may have a structure of discharging heat generated from the acoustic module 111 to the outside of the housing 170. For example, the wireless ultrasound probe 100 may include an anisotropic heat conductive member 610 and a first heat sink member 620 disposed inside the housing 170.

The first heat sink member 620 is disposed inside the heat sink portion 173 of the housing 170. With the heat sink portion 173 having the mesh structure, the first heat sink member 620 may be exposed to air and simultaneously may prevent a contact of a user. Since the first heat sink member 620 is exposed to air introduced to the inside of the heat sink portion 173, the first heat sink member 620 may discharge heat transferred from the anisotropic heat conductive member 610. The first heat sink member 620 may include a plurality of radiating pins to increase an exposed area.

The anisotropic heat conductive member 610 is disposed inside the handle portion 172. The anisotropic heat conductive member 610 may extend along the lengthwise direction (Y-direction) of the housing 170. The anisotropic heat conductive member 610 may pass through the first insulating wall 181.

The anisotropic heat conductive member 610 may be connected to the acoustic module 111. For example, the acoustic module 111 is disposed at one end of the anisotropic heat conductive member 610, and the anisotropic heat conductive member 610 contacts the acoustic module 111.

Figure 8:
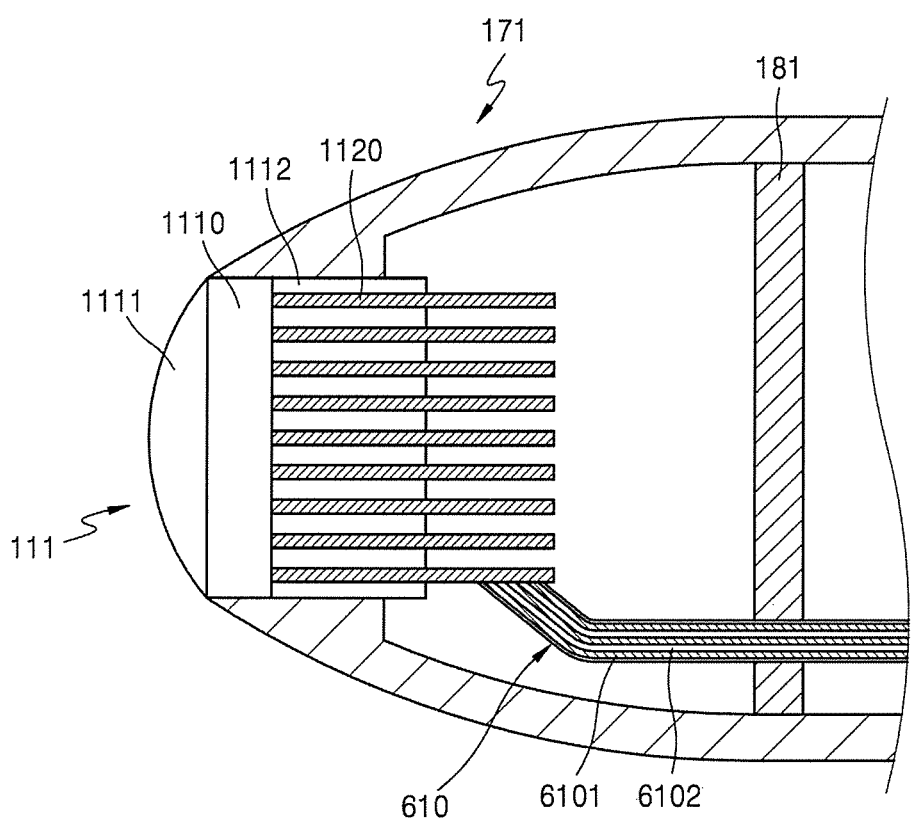
FIG. 8 is an enlarged view of a portion of FIG. 5.

FIG. 8 is an enlarged view of a portion of FIG. 5. Referring to FIG. 8, the acoustic module 111 includes a piezoelectric body 1110 configured to generate an ultrasound signal, an acoustic lens 1111 disposed in a front direction of the piezoelectric body 1110, and a backing plate 1112 disposed in a rear direction of the piezoelectric body 1110. The acoustic module 111 further includes a heat sink member 1120 connected to the piezoelectric body 1110. The arrangement and structure of the heat sink member 1120 are provided as an example, and may be modified variously to radiate heat of the acoustic module 111.

The anisotropic heat conductive member 610 may contact the heat sink member 1120. Therefore, heat generated from the piezoelectric body 1110 of the acoustic module 111 may be transferred to the anisotropic heat conductive member 610 through the heat sink member 1120.

Figure 9:
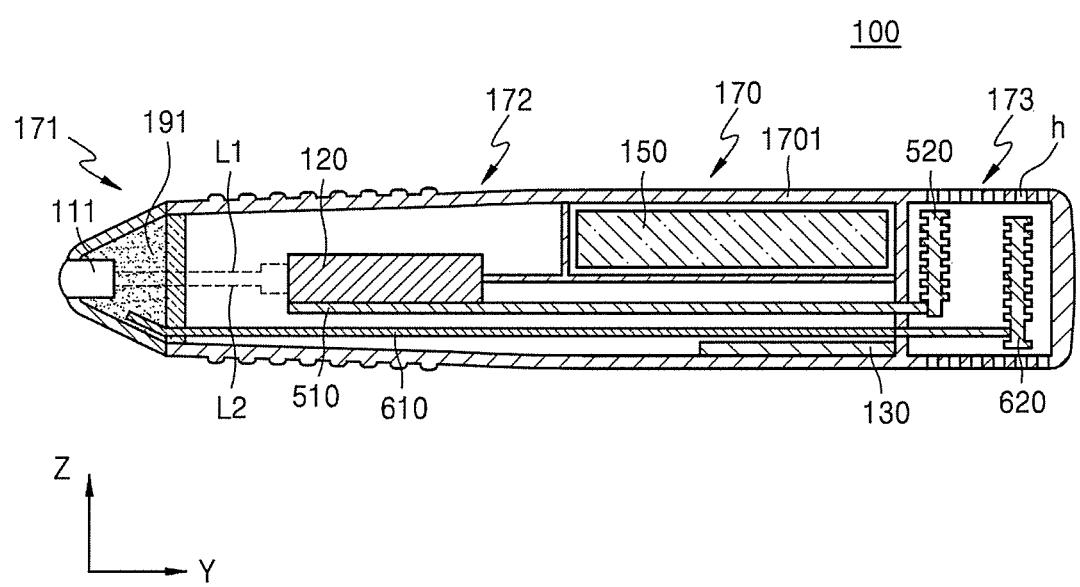
FIG. 9 is a conceptual cross-sectional view of a wireless ultrasound probe according to another embodiment.

However, the connection between the anisotropic heat conductive member 610 and the acoustic module 111 is not limited thereto, and may be modified variously as far as it is a structure which may transfer heat from the acoustic module 111 to the anisotropic heat conductive member 610. For example, as illustrated in FIG. 9, a heat conductive material 191 may be disposed between the acoustic module 111 and the anisotropic heat conductive member 610, and heat of the acoustic module 111 may be transferred to the anisotropic heat conductive member 610 through the heat conductive material 191.

Referring to FIG. 5 again, the anisotropic heat conductive member 610 is connected to the first heat sink member 620. For example, the first heat sink member 620 is disposed at the other end of the anisotropic heat conductive member 610, and the anisotropic heat conductive member 610 contacts the first heat sink member 620. Heat is transferred from the acoustic module 111 to the first heat sink member 620 through the anisotropic heat conductive member 610.

The anisotropic heat conductive member 610 may be disposed adjacent to the image processor 120 inside the handle portion 172. For example, a distance between the anisotropic heat conductive member 610 and the image processor 120 may be 10 mm or less.

The anisotropic heat conductive member 610, despite the image processor 120 of high temperature disposed adjacent thereto, may be configured to transfer heat from the acoustic module 111 to the first heat sink member 620.

For example, the anisotropic heat conductive member 610 may transfer heat in a unidirection, for example, a lengthwise direction. A heat conductivity of the anisotropic heat conductive member 610 in the lengthwise direction may be greater than a heat conductivity of the anisotropic heat conductive member 610 in a direction perpendicular to the lengthwise direction. For example, the heat conductivity of the anisotropic heat conductive member 610 in the lengthwise direction may be ten times greater or more than the heat conductivity of the anisotropic heat conductive member 610 in the direction perpendicular to the lengthwise direction. Heat is transferred in the lengthwise direction by the anisotropic heat conductive member 610 having the unidirectional heat transfer characteristic, and heat transfer in a direction perpendicular to the lengthwise direction may be blocked or limited. Here, the blocking or limiting of heat transfer denotes that a heat conductivity is 0.5 W/mK or less.

The anisotropic heat conductive member 610 is disposed such that heat is transferred in the lengthwise direction (Y-direction) of the housing 170. For example, the anisotropic heat conductive member 610 may be disposed such that the lengthwise direction of the anisotropic heat conductive member 610 corresponds to the lengthwise direction (Y-direction) of the housing 170. For example, the anisotropic heat conductive member 610 may be disposed such that the lengthwise direction of the anisotropic heat conductive member 610 is parallel to the lengthwise direction (Y-direction) of the housing 170. Heat is transferred in the lengthwise direction (Y-direction) of the housing 170 by the anisotropic heat conductive member 610, and heat transfer in the direction, for example, a height direction (Z-direction) perpendicular to the lengthwise direction (Y-direction) of the housing 170 may be blocked or limited.

If, like the wireless ultrasound probe 1 illustrated in FIGS. 6A and 6B, a wireless ultrasound probe does not include the anisotropic heat conductive member 610 and the first heat sink member 620, heat of the acoustic module 111 cannot be discharged in a rear direction. Since the image processor 120 disposed in a rear direction of the acoustic module 111 is higher temperature than the acoustic module 111, heat from the acoustic module 111 cannot be discharged in a rear direction, and rather, may be discharged in a front direction.

Also, in the case where a general heat conductive member, not the anisotropic heat conductive member 610, is used to radiate heat of the acoustic module 111, heat transfer in the direction (Z-direction) perpendicular to the lengthwise direction (Y-direction) of the housing 170 may occur. Therefore, the heat conductive member may be heated by the image processor 120 adjacent thereto, and heat from the acoustic module 111 cannot be transferred to the first heat sink member 620. Rather, the heat conductive member may serve as a path through which the acoustic module 111 is heated by the image processor 120, and thus a surface temperature of the acoustic module 111 may exceed 43° C.

However, since the wireless ultrasound probe 100 according to an embodiment employs the anisotropic heat conductive member 610, heat transfer in the direction (Z-direction) perpendicular to the lengthwise direction (Y-direction) of the housing 170 is blocked. Therefore, heat from the acoustic module 111 may be discharged to the back of the housing 170 without an interference of the image processor 120 of relatively high temperature.

Figure 10:
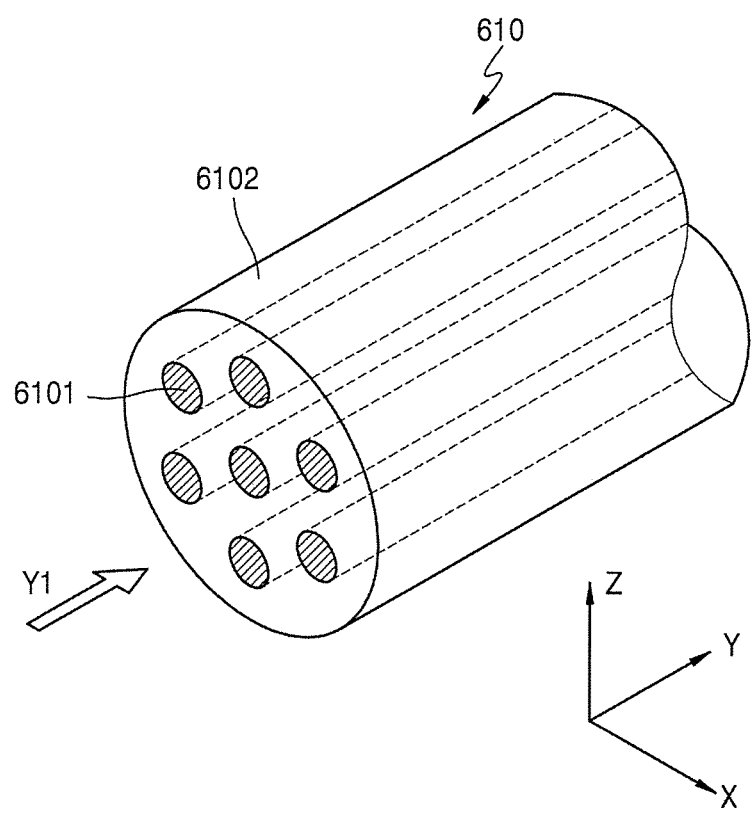
FIG. 10 is a perspective view of an anisotropic heat conductive member according to an embodiment.
Figure 11A:
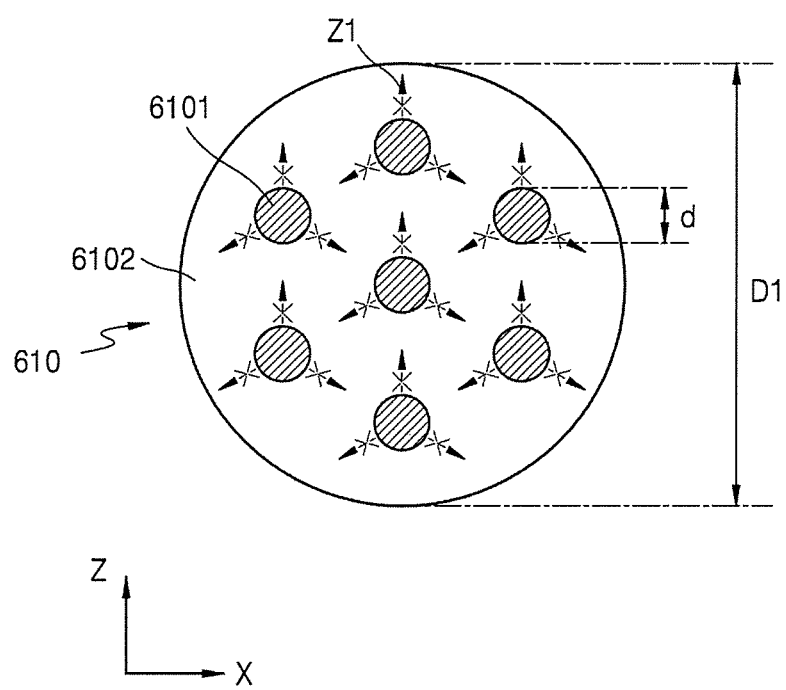
FIGS. 11A and 11B are conceptual views for explaining a heat conductive characteristic of an anisotropic heat conductive member.
Figure 11B:
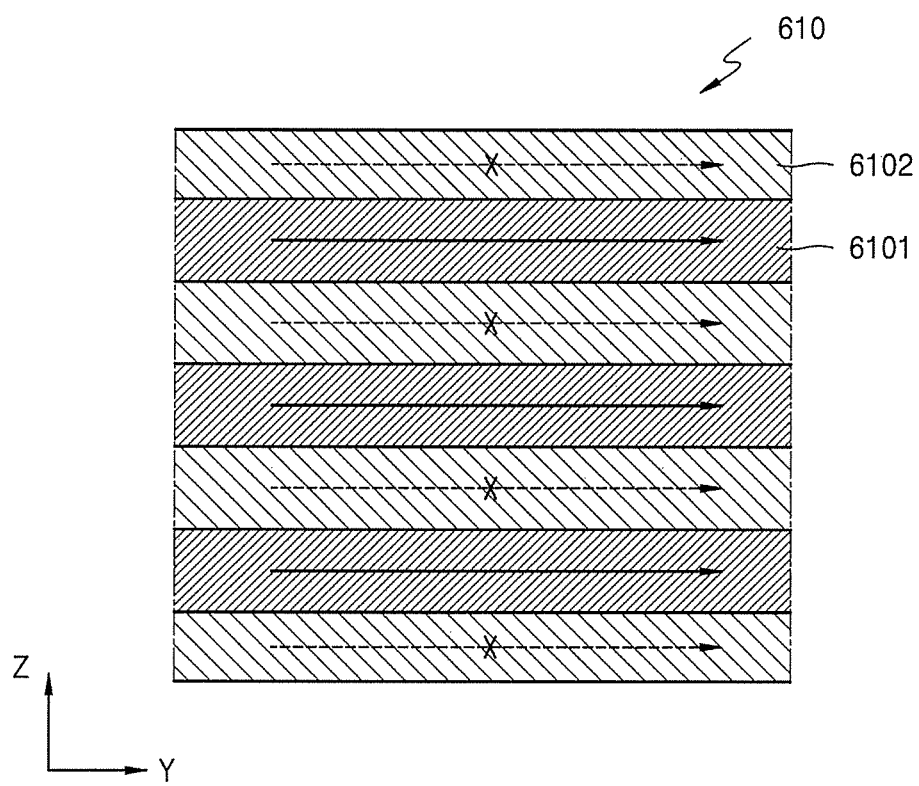

FIG. 10 is a perspective view of the anisotropic heat conductive member 610 according to an embodiment, and FIGS. 11A and 11B are conceptual views for explaining a heat conductive characteristic of the anisotropic heat conductive member 610.

Referring to FIGS. 5 and 10, the anisotropic heat conductive member 610 may include at least one heat conductive fiber 6101 and an insulating material 6102 surrounding the heat conductive fiber 6101. For example, the anisotropic heat conductive member 610 may include a plurality of heat conductive fibers 6101 and the insulating material 6102 surrounding the plurality of heat conductive fibers 6101.

A heat conductivity of the heat conductive fiber 6101 may be 100 W/mK or more. The heat conductive fiber 6101 may include at least one of gold, silver, copper, aluminium, carbon, a heat conductive alloy, a heat conductive polymer, and a superconductivity material. Here, the heat conductive fiber 6101 including carbon may be implemented in various forms, and may include at least one of carbon fiber, graphite, graphene, and a carbon nanotube.

A heat conductivity of the insulating material 6102 may be 0.3 W/mK or less. The insulating material 6102 may include epoxy, etc.

Referring to FIGS. 10, 11A, and 11B, the anisotropic heat conductive member 610 transfers heat along a lengthwise direction Y1 of the heat conductive fiber 6101. Since the insulating material 6102 is disposed around the heat conductive fiber 6101, heat transfer in a direction Z1 perpendicular to the lengthwise direction Y1 of the heat conductive fiber 6101 may be blocked. In other words, heat is transferred in the lengthwise direction Y1 in the heat conductive fiber 6101, but heat transfer in the lengthwise direction Y1 of the heat conductive fiber 6101 and the direction Z1 perpendicular thereto may be blocked in the insulating material 6102 due to a characteristic of the insulating material 6102.

A heat conductivity in the lengthwise direction Y1 of the anisotropic heat conductive member 610 may be ten times greater, more preferably, hundred times greater than a heat conductivity in the direction Z1 perpendicular to the lengthwise direction Y1 of the anisotropic heat conductive member 610. For example, the heat conductivity in the lengthwise direction Y1 of the anisotropic heat conductive member 610 may be 50 W/mK or more, and the heat conductivity in the direction Z1 perpendicular to the lengthwise direction Y1 may be 0.5 W/mK or less.

A diameter d of the heat conductive fiber 6101 may be equal to or less than several tens micrometers. For example, a diameter d of the heat conductive fiber 6101 may be 15 μm or less.

A thickness D1 or a diameter of the anisotropic heat conductive member 610 including the plurality of heat conductive fibers 6101 and the insulating material 6102 may be equal to or less than several millimeters. For example, the thickness D1 of the anisotropic heat conductive member 610 may be 5 mm or less. Since the anisotropic heat conductive member 610 has a very thin thickness D1 though having a unidirectional heat conductive characteristic in the lengthwise direction, the anisotropic heat conductive member 610 may be disposed inside a slim structure of the wireless ultrasound probe 100. Therefore, the wireless ultrasound probe 100 according to an embodiment may transfer and discharge heat from the acoustic module 111 to the rear direction of the wireless ultrasound probe 100 by using the anisotropic heat conductive member 610 though having a slim structure.

Referring to FIG. 5 again, at least a portion of the anisotropic heat conductive member 610 may be disposed between an outer wall 1701 of the housing 170 and the image processor 120. Though FIG. 5 illustrates that a space between an inner surface of the housing 170 and the image processor 120 is wide to explain the anisotropic heat conductive member 610, the space between the inner surface of the housing 170 and the image processor 120 is much narrower than the space shown in FIG. 5. For example, an interval G between an inner surface of the handle portion 172 and the heat conductive plate 510 may be several mm or less, for example, 5 mm or less.

In the case where the thickness D1 (see FIG. 9) of the anisotropic heat conductive member 610 is 5 mm or less, even though the interval G between the inner surface of the handle portion 172 and the heat conductive plate 510 is narrow, heat from the acoustic module 111 may be transferred to the rear direction of the wireless ultrasound probe 100 without increasing a height of the wireless ultrasound probe 100.

Figure 12:
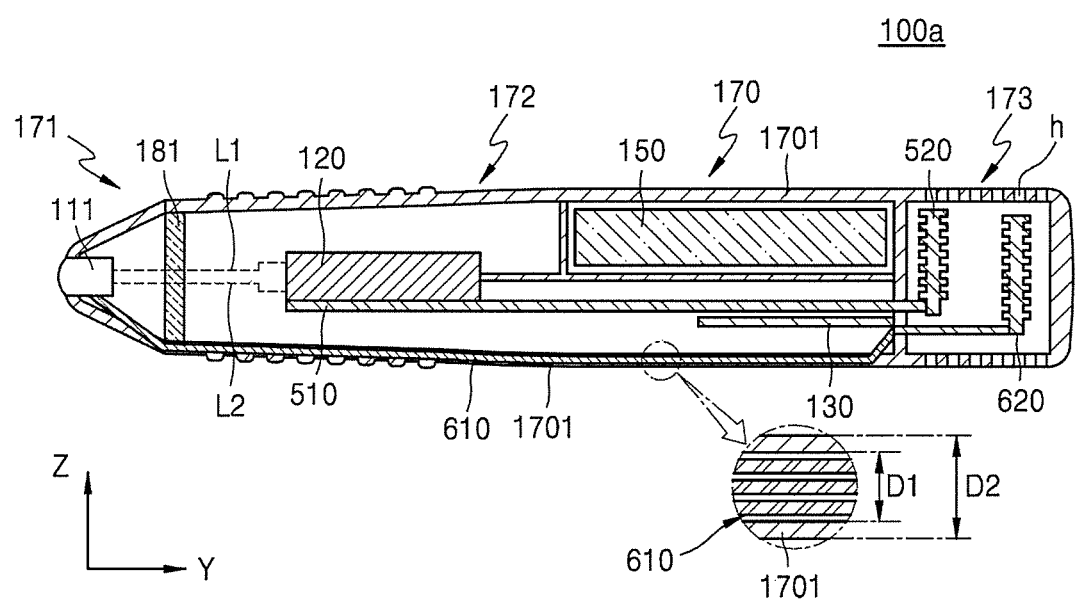
FIG. 12 is a conceptual cross-sectional view of a wireless ultrasound probe according to another embodiment.

However, the arrangement of the anisotropic heat conductive member 610 is not limited thereto. For example, in a wireless ultrasound probe 100a according to another embodiment, the anisotropic heat conductive member 610 may be inserted into the outer wall 1701 of the housing 170 as illustrated in FIG. 12. A thickness D2 of the outer wall 1701 of the housing 170 may be 5 mm or less. For example, a thickness of an outer wall of the handle portion 172 may be 5 mm or less.

Figure 13A:
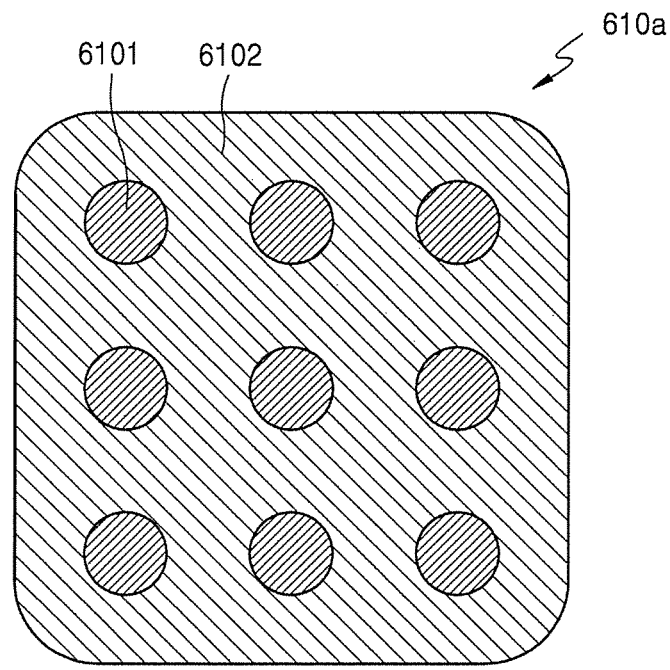
FIGS. 13A and 13B are conceptual views of a cross-sectional shape of an anisotropic heat conductive member according to another embodiment.
Figure 13B:
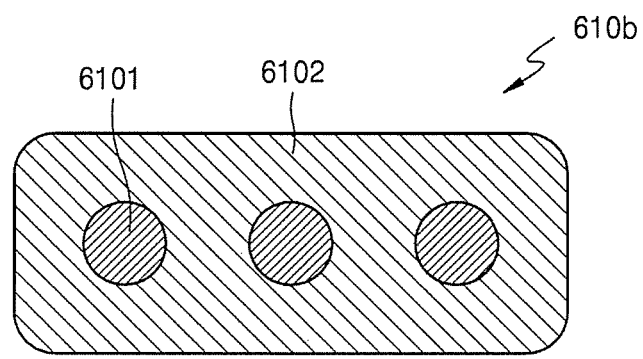

Meanwhile, the above embodiments have mainly described an example in which a cross-section of the anisotropic heat conductive member 610 is circular. However, the cross-section of the anisotropic heat conductive member 610 is not limited thereto and may be modified variously. For example, a cross-section of anisotropic heat conductive members 610a and 610b may be a rounded square as illustrated in FIG. 13A, or a rounded rectangle as illustrated in FIG. 13B.

Figure 14:
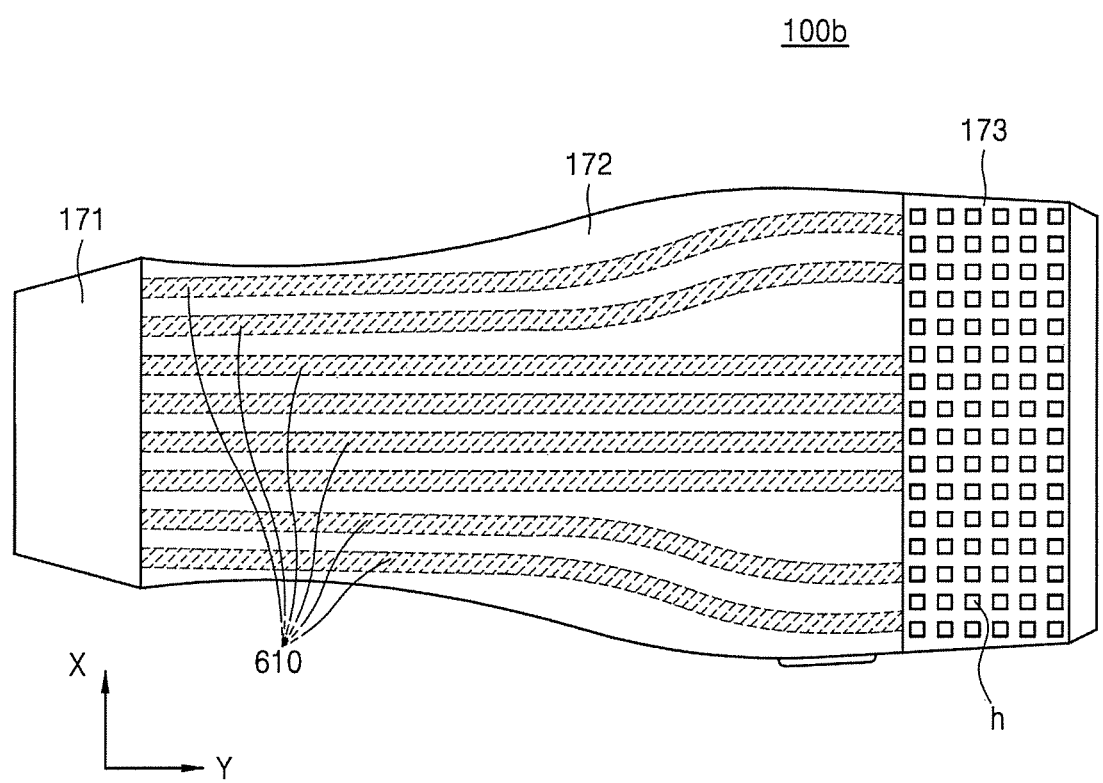
FIG. 14 is a view for explaining an example in which an anisotropic heat conductive member is disposed in a wireless ultrasound probe.

FIG. 14 is a view for explaining an example in which the anisotropic heat conductive member 610 is disposed in a wireless ultrasound probe 100b, and is a view of the wireless ultrasound probe 100b viewed from a backside. Referring to FIG. 14, the wireless ultrasound probe 100b may include the plurality of anisotropic heat conductive members 610. The plurality of anisotropic heat conductive members 610 may be spaced apart from each other in a width direction of the wireless ultrasound probe 100b, for example, an X-direction.

Figure 15:
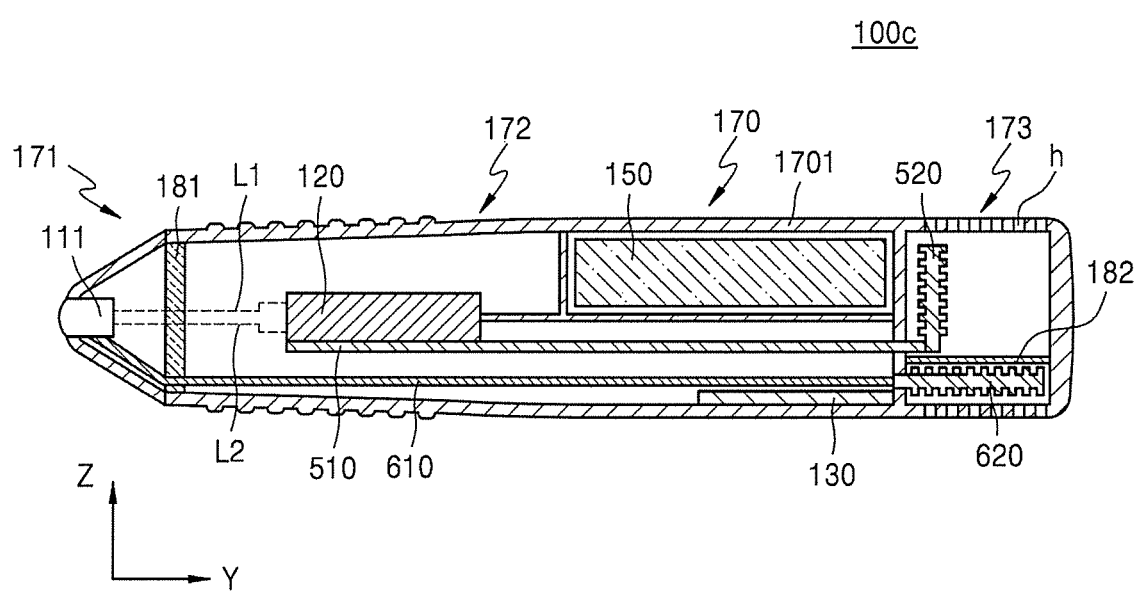
FIG. 15 is a conceptual cross-sectional view of a wireless ultrasound probe according to another embodiment.

FIG. 15 is a conceptual cross-sectional view of a wireless ultrasound probe according to another embodiment. Referring to FIG. 15, a second insulating wall 182 configured to block heat transfer between the first heat sink member 620 and the second heat sink member 520 may be disposed in the heat sink portion 173. Temperature of the second heat sink member 520 may be higher than temperature of the first heat sink member 620. The second insulating wall 182 may prevent the first heat sink member 620 from being heated by the second heat sink member 520. Besides, though not shown, the first heat sink member 620 may be spaced apart from the second heat sink member 520 by a predetermined distance to prevent heat transfer between the first heat sink member 620 and the second heat sink member 520 without installation of the second insulating wall 182.

Though the above embodiments have mainly described an example in which the ultrasound probe is the wireless ultrasound probe 100, the embodiments are not limited thereto and are readily applicable to a wired ultrasound probe.

It will be understood by those skilled in the art that various changes in form and details may be made therein without departing from the spirit and scope of the inventive concept as defined by the appended claims. The exemplary embodiments should be considered in descriptive sense only and not for purposes of limitation. Therefore, the scope of the present disclosure is defined not by the detailed description of the present disclosure but by the appended claims, and all differences within the scope will be construed as being included in the present disclosure.

The invention claimed is:
1. An ultrasound probe comprising:
a housing comprising a heat sink portion;
an acoustic module disposed inside the housing, and configured to transmit an ultrasound signal to an object and receive an echo signal reflected from the object;
an image processor disposed in a rear direction of the acoustic module inside the housing, electrically connected to the acoustic module, and configured to generate ultrasound image data from the echo signal received from the acoustic module;
a first insulating wall disposed between the acoustic module and the image processor inside the housing;
a first heat sink member disposed in a rear direction of the image processor inside the heat sink portion;
at least one anisotropic heat conductive member passing through the first insulating wall to connect the acoustic module with the first heat sink member, and configured such that a heat conductivity thereof in a lengthwise direction of the housing is greater than a heat conductivity thereof in a direction perpendicular to the lengthwise direction of the housing to transfer heat of the acoustic module to the first heat sink member,
a second heat sink member disposed in the heat sink portion;
a heat conductive plate connecting the image processor with the second heat sink member; and
a second insulating wall configured to block heat transfer between the first heat sink member and the second heat sink member, the second insulating wall disposed inside the heat sink portion.

2. The ultrasound probe of claim 1, wherein while the ultrasound probe operates, a temperature of the image processor is higher than a temperature of the acoustic module.

3. The ultrasound probe of claim 1, wherein the anisotropic heat conductive member is configured such that the heat conductivity thereof in the lengthwise direction of the housing is ten times greater than the heat conductivity thereof in the direction perpendicular to the lengthwise direction of the housing.

4. The ultrasound probe of claim 1, wherein the anisotropic heat conductive member is configured such that the heat conductivity thereof in the lengthwise direction of the housing is 50 W/mK or more, and the heat conductivity thereof in the direction perpendicular to the lengthwise direction of the housing is 0.5 W/mK or less.

5. The ultrasound probe of claim 1, wherein the anisotropic heat conductive member comprises at least one heat conductive fiber and an insulating material surrounding the at least one heat conductive fiber.

6. The ultrasound probe of claim 5, wherein a diameter of the heat conductive fiber is 15 μm or less, and a thickness of the anisotropic heat conductive member is 5 mm or less.

7. The ultrasound probe of claim 1, wherein at least a portion of the anisotropic heat conductive member is disposed between the image processor and an outer wall of the housing, or disposed inside the outer wall of the housing.

8. The ultrasound probe of claim 1, wherein the acoustic module comprises:
   a piezoelectric body configured to generate an ultrasound signal;
   an acoustic lens disposed in a front direction of the piezoelectric body;
   a backing plate disposed in a rear direction of the piezoelectric body; and
   a heat sink member configured to discharge heat of the piezoelectric body,
   wherein one end of the anisotropic heat conductive member contacts the heat sink member.

9. The ultrasound probe of claim 1, further comprising a heat conductive material disposed between the acoustic module and the anisotropic heat conductive member.

10. The ultrasound probe of claim 1, wherein the heat sink portion has a mesh structure through which air flows in/out, and the first heat sink member is disposed inside the heat sink portion.

11. The ultrasound probe of claim 1, wherein the anisotropic heat conductive member is provided as a plurality of anisotropic heat conductive members, and the plurality of anisotropic heat conductive members are spaced apart from each other in a width direction of the housing.

12. The ultrasound probe of claim 1, wherein the ultrasound probe comprises a wireless ultrasound probe.

13. An ultrasound diagnosis system comprising the ultrasound probe of claim 1.

14. The ultrasound diagnosis system of claim 13, wherein while the ultrasound probe operates, a temperature of the image processor is higher than a temperature of the acoustic module.

15. The ultrasound diagnosis system of claim 13, wherein the anisotropic heat conductive member is configured such that the heat conductivity thereof in the lengthwise direction of the housing is ten times greater than the heat conductivity thereof in the direction perpendicular to the lengthwise direction of the housing.

16. The ultrasound diagnosis system of claim 13, wherein the anisotropic heat conductive member is configured such that the heat conductivity thereof in the lengthwise direction of the housing is 50 W/mK or more, and the heat conductivity thereof in the direction perpendicular to the lengthwise direction of the housing is 0.5 W/mK or less.

17. The ultrasound diagnosis system of claim 13, wherein the anisotropic heat conductive member comprises at least one heat conductive fiber and an insulating material surrounding the at least one heat conductive fiber.

18. The ultrasound diagnosis system of claim 17, wherein a diameter of the heat conductive fiber is 15 μm or less, and a thickness of the anisotropic heat conductive member is 5 mm or less.

* * * * *